United States Patent [19]

Evans et al.

[11] Patent Number: 5,230,884

[45] Date of Patent: Jul. 27, 1993

[54] AEROSOL FORMULATIONS INCLUDING PROTEINS AND PEPTIDES SOLUBILIZED IN REVERSE MICELLES AND PROCESS FOR MAKING THE AEROSOL FORMULATIONS

[75] Inventors: Richard M. Evans, Westwood, Mass.; Stephen J. Farr, Llandaf, Wales

[73] Assignee: University of Wales College of Cardiff, United Kingdom

[21] Appl. No.: 834,111

[22] Filed: Feb. 11, 1992

Related U.S. Application Data

[63] Continuation-in-part of Ser. No. 580,926, Sep. 11, 1990, abandoned.

[51] Int. Cl.$^5$ .................... A61K 9/12; A61K 9/127
[52] U.S. Cl. ........................... 424/45; 424/43; 424/45 D; 514/3; 514/866; 514/937
[58] Field of Search .................. 424/45, 43, 450; 514/937

[56] References Cited

U.S. PATENT DOCUMENTS 4,814,161  3/1989  Jinks et al. ..................... 424/45

FOREIGN PATENT DOCUMENTS 0372777  11/1989  United Kingdom .

OTHER PUBLICATIONS

Singleterry et al., J. Am. Oil Chem. Soc., 32:446–452 (1955).
Byron, Ad. Drug Delivery Rev., 5:107–132 (1990).
Evans et al., J. Aerosol Sci. 20:1309 (1989).
Evans et al., J. Pharm. Pharmacol. 41:36 (1989).
Evans et al., J., Pharm. Pharmacol. 40:76 (1988).
Luisi et al., Biochimica Biophysica Acta., 947:209–246, (1988).
Appendix: Respiratory Drug Delivery, Peter Byron, Ed., CRC Press, Inc., 1990, pp. 249–253.

*Primary Examiner*—Thurman K. Page
*Assistant Examiner*—Raj Bawa
*Attorney, Agent, or Firm*—Whitham and Marhoefer

[57] ABSTRACT

Highly purified and recombinantly produced polypeptides and proteins can be provided to a patient to treat systemic disorders using a metered dose inhaler (MDI). The polypeptides and proteins are solubilized in reverse micelles formed from the surfactant in the MDI propellant. By controlling the molar ratio of water to surfactant, the amount of polypeptide or protein solubilized in the reverse micelles can be controlled, thereby providing an accurate dosing mechanism. In addition, controlling the molar ratio of water to surfactant also can adjust the size and shape of the reverse micelles which will affect the degree and rate of penetration of the lung mucosa for delivery of the drugs to the patient's blood stream. Proteins which may particularly benefit from the solubilization and systemic delivery process include calcitonin, oxytocin, and insulin.

36 Claims, 2 Drawing Sheets

| Mol. Water per Mol. Lecithin | Molar Mass M | $D_0^1$ $m^2 s^{-1} \times 10^{11}$ | Intrinsic Viscosity $[\eta]$ | Ellipsoid shape | Axial$^2$ ratio | Length$^3$ nm a | b g solvent g solute |
|---|---|---|---|---|---|---|---|
| 0.90 | 1.36 | 6.51 | 3.97 | oblate | 1.41 | 3.87 | 0.82 |
| 1.75 | 1.17 | 6.63 | 4.40 | oblate | 1.40 | 3.82 | 1.08 |
| 2.61 | 1.30 | 6.83 | 2.78 | sphere | 1.00 | 4.70 | 1.33 |
| 3.46 | 1.92 | 6.72 | 8.56 | prolate | 0.45 | 7.69 | 2.60 |
| 4.32 | 3.45 | 6.18 | 28.01 | prolate | 0.13 | 14.45 | 2.76 |
| 5.17 | 3.19 | 5.91 | 79.70 | prolate | 0.07 | 18.34 | 3.69 |

[1] Diffusion Coefficient (Do) measured by photon correlation spectroscophy
[2] Axial Ratio of length to width
[3] Length of the reverse micelle in nanometers

AEROSOL FORMULATIONS INCLUDING PROTEINS AND PEPTIDES SOLUBILIZED IN REVERSE MICELLES AND PROCESS FOR MAKING THE AEROSOL FORMULATIONS

CROSS-REFERENCE TO RELATED PATENT APPLICATIONS

This patent application is a continuation-in-part (CIP) of the co-pending U.S. patent application Ser. No. 07/580,926, filed Sep. 11, 1990, now abandoned and that patent application is herein incorporated by reference.

DESCRIPTION

BACKGROUND OF THE INVENTION

1. Field of the Invention

The present invention generally relates to metered dose inhalers (MDIs) and, more particularly, to the solubilization and delivery of polypeptides and proteins to the lungs.

2. Description of the Prior Art

A metered dose inhaler (MDI) typically comprises a canister under pressure fitted with a metering valve where the canister is filled with an aerosol formulation that includes a drug dissolved or dispersed in a propellant together with a surfactant. Nebulizers are devices which include a dry powder drug and a mechanical or electronic means to generate and deliver a fine mist of the drug. MDIs and nebulizers have been used for many years to treat pulmonary disorders such as asthma. Currently, several different types of drugs are routinely provided to patients using MDIs in the treatment of pulmonary disorders. Examples of these types of drugs include β-agonists such as albuterol (salbutamol), isoproterenol, ephedrine, epinephrine, salmeterol, terbutaline, and norepinephrinec corticosteroids such as triamcinolone acetonide, beclomethasone diprionate, dexamethasone, and aldosterone, allergic mediators such as cromolyn sodium, antibiotics, and anticholinergics. While the lungs have been recognized as a port to the bloodstream (e.g., through the lung mucosa), very little work has been performed in the area of using an MDI or nebulizer to deliver systemically active polypeptides or proteins to a patient.

SUMMARY OF THE INVENTION

It is therefore an object of the invention to provide a method of delivering purified or recombinantly produced polypeptides or proteins to a patient wherein the lung is used as a port to the bloodstream.

It is another object of the invention to provide a metered dose inhaler with purified or recombinantly produced polypeptides or proteins solubilized in reverse micelles.

According to the invention, it has been recognized that the lungs are a convenient port of entry into a patient's bloodstream. The lung is filled with many capillaries. An extremely thin membrane barrier called the mucosa separates lung air from blood. The intimate relationship of lung air with the blood allows for the bodies, rapid exchange of $O_2$ and $CO_2$. This invention takes advantage of the intimate relationship of lung air with blood by passing a purified or recombinantly produced polypeptide or protein through the mucosa directly into the patient's blood stream. In order to deliver the polypeptides or proteins to the patient's lungs, an MDI is provided which includes the polypeptides or proteins solubilized in reverse micelles formed from soybean lecithins, egg yolks, or other suitable surfactants. Adjusting the molar ratio of water to surfactant allows control of both the amount of polypeptide or protein which is solubilized and the size and shape of the reverse micelle. Therefore, adjusting the water content of the reverse micelle allows for both dosage control (e.g., the amount of polypeptide or protein solubilized) and lung mucosa penetration with resulting delivery to the blood stream (e.g., the size and shape of the reverse micelle may affect the degree and rate of passage through the lung mucosa).

BRIEF DESCRIPTION OF THE DRAWINGS

The foregoing and other objects, aspects and advantages will be better understood from the following detailed description of a preferred embodiment of the invention with reference to the drawings, in which:

FIG. 1 is a table presenting spectrophotometric and viscometric data which demonstrate that the shape of a reverse micelle can be controlled by regulating the molar ratio of moles of water to moles of surfactant;

FIG. 2 is a graph showing the solubility of a drug compound within a reverse micelle core is affected by both the molar ratio of water to surfactant and the form of the drug compound.

DETAILED DESCRIPTION OF THE PREFERRED EMBODIMENTS OF THE INVENTION

The traditional method of delivering systemically active drug compounds such as purified or recombinantly produced polypeptides or proteins to a patient is by injection into a vein. However, after injection, a large portion of the polypeptides or proteins are metabollized in the patient's liver and kidneys prior to reaching their intended site of activity. This phenomena is often referred to as "first pass metabolism". This particular invention is distinctly different from the traditional injection method in that the polypeptides or proteins are administered to the patient via inhalation. By delivering the polypeptides or proteins deeply into the lungs to a point where they can pass through the lung mucosa into the blood stream, first pass metabolism will be significantly reduced because the activity of enzymes found in the lungs is generally lower than the corresponding enzymes in the liver (see, Fielding et al., *J. Pharmacol. Exp. Ther.*, 236:97 (1986) and Roth, *Clin. Physiol. Biochem.*, 6:66 (1985)).

Delivery of the polypeptides or proteins is best accomplished using an MDI. A preferred MDI formulation is a colloidal dispersion comprised of a propellant containing reverse micelles made from the surfactant. As is described in our co-pending patent application Ser. No. 580,926, filed Sep. 11, 1990, the reverse micelles are preferably formed from glycerol phosphatide surfactants including phosphatidyl choline (lecithin), phosphatidyl ethanolamine (cephalin), phosphatidyl inositol, phosphatidyl serine, and diphosphatidyl glycerol. Other surfactant compounds may also be used including sorbitan mono and tri-oleates (Span 80 and 85), diolein (DO), oleic acid, and phosphatidic acid. A cosolubilizer such as polyethylene glycol may also be included. Likewise, combinations of surfactants could be used. A particularly suitable surfactant for making the reverse micelles is soya bean lecithin and a suitable grade is Epikuron 200, available from Lucas-Meyer and which has a phosphatidyl choline content in excess of 95%. The surfactant concentration of the MDI formulation should range between 0.05% and 2.5% weight in volume (w/v) and most preferably between 0.5% and 2% w/v with the remaining volume component being the propellant.

The propellant can be any or a combination of the well known chlorofluorocarbon (freon) propellants including $CCl_3F$ (Freon 11 or CFC-11), $CCl_2F_2$ (Freon 12 or CFC-12), and $CClF_2$-$CClF_2$ (Freon 114 or CFC-114). However, there has recently been much emphasis on using more ozone friendly propellants such as 1,1,1,2-tetrafluoroethane (HFC-134a), hydrocarbons (propane, butane, isobutane, etc.), fluorocarbons (perfluoropentane), dimethyl ether, or the like, in MDI applications. The copending U.S. patent application Ser. No. 07/655,668, filed Feb. 14, 1991, now U.S. Pat. No. 5,182,097, demonstrates the utility of a wide number of non-CFC propellants and that patent application is incorporated herein by reference.

This patent application extends our earlier work in that it has been recognized that drugs with systemic activity as opposed to pulmonary activity, such as purified or recombinantly produced polypeptides and proteins, could be advantageously provided to a patient via inhalation. The preferred MDI formulations are prepared by first purifying and drying the surfactant and the polypeptide or protein, then combining the dried surfactant and the polypeptide or protein in an MDI cannister with a precisely determined quantity of water which will solubilize the polypeptide or protein within the reverse micelles that will form from the surfactant, and filling the remainder of the MDI cannister with propellant The use of reverse micelles for the solubilization of therapeutic peptides and proteins is appropriate because reverse micelles are amphoteric in nature and thus afford hydrophilic and hydrophobic domains for the solubilization of polymeric materials such as polypeptides. Moreover, the intercalation of peptides within the microenvironment of the reverse micelle will provide the appropriate structure for solubilization without alteration of the tertiary conformation of the therapeutic polypeptide. It has been recently demonstrated that enzymes solubilized inside the reversed micelles formed by the surfactant present in organic solvents retain their complete catalytic activity and substrate specificity (see, Srivastava, *Biotechnology Bioeng.*, 29 (1987) 901). The enzyme molecules entrapped in the reversed micelles avoids direct contact with an unfavorable organic medium and thus they are protected against denaturation. The retention, by solubilized proteins, of their native conformation during the transfer process and the fact that they remain in an active form when incorporated into reversed micelles makes their delivery by MDIs very attractive.

If lecithin is used as the surfactant, a particularly preferred method for purifying lecithin is column chromatography on aluminum oxide (neutral) using a chloroform/methanol mixture as eluant. If a conventional propellant blend of CFC-11 and CFC-12 is to be used, the CFC-11 can be added to the canister to excess at 4° C. and allowed to evaporate till a predetermined weight is obtained, followed by crimping a metering valve into position on the canister and filling the remainder of the canister with CFC-12 by pressure filling as described in Sanders, *Handbook of Aerosol Technology*, Van Nostrand Reinhold, New York, 1979.

Particularly preferred polypeptides and proteins which can benefit from being formulated in an aerosol formulation with reverse micelles include oxytocin, calcitonin, and insulin Oxytocin is one of the polypeptide hormones of the posterior lobe of the pituitary gland and has approximately nine amino acid residues. Oxytocin stimulates rhythmic contractions of the uterus and is used at the end of pregnancy. Calcitonin is a single chain polypeptide hormone having 32 amino acid residues which plays a role in calcium and bone metabolism. Insulin is a larger protein used in the management of diabetes. Oxytocin, calcitonin, and insulin are commercially available from a variety of sources in purified or recombinantly produced form.

As is discussed in Evans et al., *J. Pharm. Pharmacol.*, 40:7P (1988), there is an upper limit for the incorporation of water in the reverse micelles before phase separation occurs which depends on the characteristics of the surfactant. The upper limit molar ratio of moles of water to moles of surfactant is typically between 5:1 and 20:1. While Epikuron 200 is reasonably pure, it is typically supplied with 1–3% associated water. Other surfactants also are generally supplied with associated water molecules. Therefore, if the surfactant is not dried prior to adding water to form the reverse micelle MDI formulation, there is a danger that the added water will cause phase separation. Hence, it is recommended that the surfactant be dried to a molar ratio of moles of water to moles of surfactant ranging from 0.5:1 to 1:1 prior to adding water and drug in the MDI canister. Moreover, it is believed that drying the surfactant prior to adding water will allow for more precise control of the molar ratio of water to surfactant when water is added. Drying can be accomplished by repetitively washing the surfactant in dry methanol heated to 60° C. followed by evaporation of the methanol by rotary vacuum evaporation similar to the description in Van Mil et al., *J. Colloid Interface Sci.*, 98:61 (1984). Subsequently, during the water addition stage, the amount of water added preferably creates a molar ratio of moles of water to moles of surfactant ranging from 0.9 to 5.6:1, and most preferably between 0.9:1 and 2:1.

Figure 2:
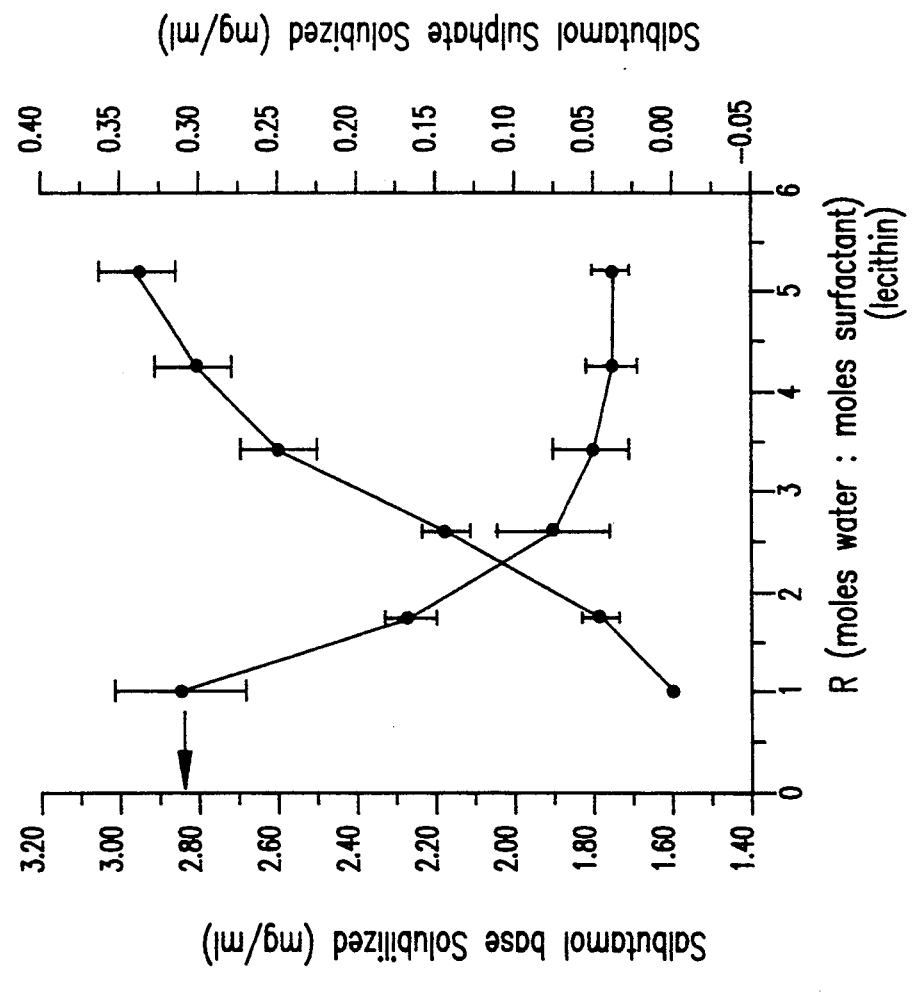

FIG. 1 presents light scattering, spectrophotometric and viscometric data from a soya lecithin/trichlorotrifluoroethane (CFC-113) system where the molar ratio of the water per mole of lecithin (Epikuron 200) varied from approximately 1:1 to 5:1 As described above, the system was prepared by combining the dried lecithin with water and adding CFC-113. Absolute water content determinations were made using a Kari-Fischer Titrater AF5 available from Baird and Tatlock. FIG. 2 shows a clear change in micellular shape with the molar ratio. The reverse micelles are oblate (dish shaped) when the molar ratio of water to lecithin is below 2.6, spherical when the molar ratio is approximately 2.6, and prolate (cigar shaped) when the molar ratio is above 2.6. The size and shape of the reverse micelles will play a key role in both the delivery of the micelles deeply into the lung and the subsequent penetration through the lung mucosa into the blood stream. Therefore, by adjusting the size and shape of reverse micelles containing purified or recombinantly produced polypeptides or proteins can be used as a means to control the degree and rate of delivery of the polypeptides and proteins to the patient's blood stream.

FIG. 2 shows that the amount of a drug which can be solubilized in the reverse micelles is dependent on the molar ratio of the moles of water to the moles of lecithin. Several 2% w/v solutions of purified and dried lecithin in CFC-113 were prepared in small conical flasks containing varying quantities of water chosen to adjust the molar ratio of water to lecithin to range between 1:1 and 5:1. The flasks were stoppered and allowed to equilibrate for one day. Subsequently, excess dried salbutamol base or dried salbutamol sulphate was added to the flasks and the flasks were resealed for one week. During both the initial and final equilibration periods, the flasks were shaken in a water bath at room temperature. At the end of the seven day period, the contents of the flasks were filtered through a 0.1 μm cellulose acetate/nitrate filter (25 mm, Millipore) using a microbiological clearing assembly that fit into a 20 ml glass syringe Small additional volumes of CFC-113 were used to wash through the filter and adjust for the small losses of which had occurred in storage. Drug solubility in the filtrate was assessed using photometric assay procedures. FIG. 2 shows that the solubilizing capacity of the micellular system decreased for the salbutamol base with increasing molar ratios of water to lecithin. This can be attributed to competitive hydrogen bonding between the drug and water at the choline head groups Conversely, there was an increase in the solubility of the sulphate salt with an increase in the molar ratio. This can be attributed to an increase in the micellar core polarity at higher molar ratios of moles of water to moles of lecithin. This was confirmed by a red shift in the emission peak of anilinonaphthalene-sulfonic acid (ANSA) to values similar to those in bulk water.

From FIG. 2, it can be seen that the water content added in the creation of the reverse micelles can play an extremely important role in regulating the amount of any drug which is solubilized in a reverse micelle which will subsequently be delivered to a patient. Hence, the dosage of particular drugs, such as polypeptides and proteins, including calcitonin, oxytocin, and insulin, which will be delivered by an MDI can be regulated by controlling the amount of water added to the surfactant in the preparation of the reverse micelle formulation. For calcitonin, oxytocin, and insulin, it is recommended that the molar ratio of water to surfactant range between 0.9:1 and 5.6:1, and most preferably between 0.9:1 and 2:1., where the form (e.g., salt or free base) of the peptide or protein will affect its solubility in the reverse micelles. Therefore, the ultimate deliverable dosage of the polypeptide or protein can be controlled by adjusting the molar ratio of water to surfactant in accordance with the form of the polypeptide or protein in order to increase or reduce solubilization within the reverse micelle. The pH of the hydrophilic center of the reverse micelle can also be altered to increase solubility and chemical stability. For example, insulin demonstrates optimum solubility at pH 4; therefore, adjusting the pH of the reverse micelles by adding appropriate amounts of acid buffers will help increase the solubility of insulin.

While the invention has been described in terms of its preferred embodiments, those skilled in the art will recognize that the invention can be practiced with modification within the spirit and scope of the appended claims.

We claim:

1. An aerosol formulation for delivery of insulin to a patient's lungs, comprising:
   at least ninety percent by weight of a propellant;
   less than ten percent by weight of insulin;
   up to 5% weight in volume of a surfactant; and
   an amount of water associated with said surfactant which results in a molar ratio of aqueous fluid to surfactant ranging from approximately 1:1 to 20:1, said surfactant being present as reverse micelles dispersed in said propellant, said aqueous fluid associated with said surfactant having a pH less than 5.5, said insulin being solubilized in said reverse micelles.

2. An aerosol formulation as recited in claim 1 wherein said water associated with said surfactant has a pH of approximately 4.

3. An aerosol formulation as recited in claim 1 wherein said reverse micelles have an oblate shape.

4. An aerosol formulation as recited in claim 1 wherein said reverse micelles have a prolate shape.

5. An aerosol formulation as recited in claim 1 wherein said reverse micelles have a spherical shape.

6. An aerosol formulation as recited in claim 1 wherein said surfactant is selected rom the group consisting of phosphatidyl choline, phosphatidyl ethanolamine, phosphatidyl inositol, phosphatidyl serine, diphosphatidyl glycerol, sorbitan mono- and tri-oleats, diolein, oleic acid, and phosphatidic acid.

7. An aerosol formulation as recited in claim 1 wherein surfactant is a combination of two or more compounds.

8. An aerosol formulation as recited in claim 1 wherein said propellant includes a gas selected from the group consisting of n-butane, isobutane, perfluoropentane, trichlorofluoroethane, dichlorotetrafluoroethane, dichlorofluoroethane, dichlorodifluoromethane, 1,1,1,2-tetrafluoroethane, propane, dimethyl ether, perfluoropropane, and heptafluoropropane.

9. A method of preparing an aerosol formulation for delivery of peptides and proteins to a patient's lungs, comprising the steps of:
   drying a surfactant from which reverse micelles can be formed; and
   mixing said surfactant with a peptide or protein, an amount of water, and a propellant to form reverse micelles of said surfactant in said propellant which incorporate said peptide or protein, said surfactant being present in an amount less than five percent weight in volume, said peptide or protein being present in an amount less than ten percent by weight, said propellant being present in an amount of at least ninety percent by weight, and said amount of water resulting in a molar ratio of water to surfactant ranging from approximately 1:1 to 20:1.

10. A method as recited in claim 9 wherein said amount of water used in said mixing step results in a molar ratio of water to surfactant ranging from 0.9:1 to 5.6:1.

11. A method as recited in claim 9 wherein said surfactant is present in an amount ranging between 0.5 and 2.5 percent weight in volume.

12. A method as recited in claim 9 wherein said drying step reduces an amount of associated water from said surfactant to yield a molar ratio of water to surfactant of 0.5:1 to 1:1.

13. A method as recited in claim 9 wherein said amount of water in said mixing step results in reverse micelles of an oblate shape.

14. A method as recited in claim 9 wherein said amount of water in said mixing step results in reverse micelles of a spherical shape.

15. A method as recited in claim 9 wherein said amount of water in said mixing step results in reverse micelles of a prolate shape.

16. A method as recited in claim 9 further comprising the step of adjusting the pH of said amount of water.

17. A method of preparing an aerosol formulation for delivery of peptides and proteins to a patient's lungs, comprising the steps of:

drying a surfactant from which reverse micelles can be formed; and mixing said surfactant with a peptide or protein, an amount of water, and a propellant to form reverse micelles of said surfactant in said propellant which incorporate said peptide or protein, said surfactant being present in an amount less than five percent weight in volume, said peptide or protein having a concentration in said propellant ranging from 0.025 mg/ml to 4.0 mg/ml, and said amount of water resulting in a molar ratio of water to surfactant ranging from approximately 1:1 to 20:1.

18. A method as recited in claim 17 wherein said amount of water used in said mixing step results in a molar ratio of water to surfactant ranging from 0.9:1 to 5.6:1.

19. A method as recited in claim 17 wherein said surfactant is present in an amount ranging between 0.5 and 2.5 percent weight in volume.

20. A method as recited in claim 17 wherein said drying step reduces an amount of associated water from said surfactant to yield a molar ratio of water to surfactant of 0.5:1 to 1:1.

21. A method as recited in claim 17 wherein said amount of water in said mixing step results in reverse micelles of an oblate shape.

22. A method as recited in claim 17 wherein said amount of water in said mixing step results in reverse micelles of a spherical shape.

23. A method as recited in claim 17 wherein said amount of water in said mixing step results in reverse micelles of a prolate shape.

24. A method as recited in claim 17 wherein said propellant includes a gas selected from the group consisting of n-butane, iosbutane, perfluoropentane, trichlorofluoromethane, dichlorotetrafluoroethane, dichlorofluoroethane, dichlorofluoromethane, 1,1,1,2-tetrafluoroethane, propane, dimethylether, pefluoropropane, and heptafluoropropane.

25. A method as recited in claim 17 wherein said surfactant is selected from the group consisting of phosphatidyl choline, phosphatidyl ethanolamine, phosphatidyl inositol, phosphatidyl serine, diphosphatidyl glycerol, sorbitan mono- and tri-oleates, diolein, oleic acid, and phosphatidic acid.

26. A method as recited in claim 17 further comprising the step of adjusting the pH of said amount of water.

27. A method of preparing an aerosol formulation for delivery of peptides and proteins to a patient's lungs, comprising the steps of:

combining a surfactant with a peptide or protein and a propellant, said surfactant being present in an amount less than 5 percent weight in volume, said peptide or protein having a concentration in said propellant ranging from 0.025 mg/ml to 4.0 mg/ml; and adjusting an amount of water associated with said surfactant to solubilize said peptide or protein in reverse micelles formed from said surfactant and dispersed within said propellant, said amount of water being adjusted to a molar ratio of water to surfactant of up to 20:1.

28. A method as recited in claim 27 wherein said step of adjusting yields reverse micelles that have a prolate shape.

29. A method as recited in claim 27 wherein said step of adjusting yields reverse micelles that have an oblate shape.

30. A method as recited in claim 27 wherein said step of adjusting yields reverse micelles that have a spherical shape.

31. A method as recited in claim 27 further comprising the step of adjusting the pH of said amount of water.

32. A method of preparing an aerosol formulation for delivery of peptides and proteins to a patient's lungs, comprising the steps of:

combining a surfactant with a peptide or protein and a propellant, said surfactant being present in an amount less than 5 percent weight in volume, said peptide or protein being present in an amount less than ten percent by weight, said propellant being present in amount of at least ninety percent by weight; and adjusting an amount of water associated with said surfactant to solubilize said peptide or protein in reverse micelles formed from said surfactant and dispersed within said propellant, said amount of water being adjusted to a molar ratio of water to surfactant of up to 20:1.

33. A method as recited in claim 32 wherein said step of adjusting yields reverse micelles that have a prolate shape.

34. A method as recited in claim 32 wherein said step of adjusting yields reverse micelles that have an oblate shape.

35. A method as recited in claim 32 wherein said step of adjusting yields reverse micelles that have a spherical shape.

36. A method as recited in claim 32 further comprising the step of adjusting the pH of said amount of water.

* * * * *